(12) United States Patent
Hémery et al.

(10) Patent No.: US 10,093,643 B2
(45) Date of Patent: Oct. 9, 2018

(54) METHOD FOR SYNTHESIZING CYCLIC CARBONATES

(71) Applicants: Henkel AG & Co. KGaA, Duesseldorf (DE); Henkel IP & Holding GmbH, Duesseldorf (DE)

(72) Inventors: Thérèse Hémery, Duesseldorf (DE); Hans-Georg Kinzelmann, Pulheim (DE); Rosa Maria Sebastián Pérez, Barcelona (ES); Jordi Marquet Cortés, Barcelona (ES); Yongxia Wang, Bridgewater, NJ (US); Jorge Aguilera, Barcelona (ES)

(73) Assignee: Henkel AG & Co. KGaA and Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 15/812,437

(22) Filed: Nov. 14, 2017

(65) Prior Publication Data
US 2018/0065948 A1    Mar. 8, 2018

Related U.S. Application Data

(63) Continuation of application No. PCT/EP2016/061357, filed on May 20, 2016.

(30) Foreign Application Priority Data

May 27, 2015 (EP) .................... 15169447

(51) Int. Cl.
| | | |
|---|---|---|
| *C07D 317/08* | (2006.01) | |
| *C07D 317/36* | (2006.01) | |
| *B01J 21/08* | (2006.01) | |
| *B01J 23/04* | (2006.01) | |
| *B01J 27/08* | (2006.01) | |
| *C08G 64/34* | (2006.01) | |

(52) U.S. Cl.
CPC .......... *C07D 317/36* (2013.01); *B01J 21/08* (2013.01); *B01J 23/04* (2013.01); *B01J 27/08* (2013.01); *C08G 64/34* (2013.01)

(58) Field of Classification Search
CPC ...... C07D 317/36; C08G 59/14; C08G 64/34; B01J 21/08; B01J 27/08; B01J 23/04
USPC ...................................................... 549/230
See application file for complete search history.

(56) References Cited

U.S. PATENT DOCUMENTS

| | | | |
|---|---|---|---|
| 4,835,289 A | 5/1989 | Brindöpke | |
| 6,258,962 B1 | 7/2001 | Buchanan et al. | |
| 6,870,004 B1 | 3/2005 | Nguyen et al. | |
| 7,232,877 B2 | 6/2007 | Figovsky et al. | |
| 7,645,831 B2 | 1/2010 | Slark et al. | |
| 8,118,968 B2 | 2/2012 | Moeller et al. | |
| 8,324,145 B2 | 12/2012 | Warkotsch et al. | |

FOREIGN PATENT DOCUMENTS

DE           3600602 A1    7/1987

OTHER PUBLICATIONS

Brenntag, Epikote 1001×75/ epoxy resin, Technical Specification, 2013, p. 1. (Year: 2013).*
International Search Report for International PCT Patent Application No. PCT/EP2016/061357 dated Jul. 5, 2016.
Cao et al., The Role of Inorganic Oxide Supports in Synthesis of Cyclic Carbonates from Carbon Dioxide and Epoxides, Chinese Journal of Catalysis, 2012, pp. 416-424, vol. 33.
Song et al., Synthesis of cyclic carbonates from epoxides and CO2 catalyzed by potassium halide in the presence of 3-cyclodextrin, Green Chemistry, 2008, pp. 1337-1341, vol. 10.
Motokura et al., Silica-supported aminopyridinium halides for catalytic transformations of epoxides to cyclic carbonates under atmospheric pressure of carbon dioxide, Green Chemistry, 2009, pp. 1876-1880, vol. 11.
Yamaguchi et al., Mg—Al Mixed Oxides as Highly Active Acid—Base Catalysts for Cycloaddition of Carbon Dioxide to Epoxides, J. Am. Chem. Soc., 1999, pp. 4526-4527, vol. 121, No. 18.
Kihara et al., Catalytic Activity of Various Salts in the Reaction of 2,3-Epoxypropyl Phenyl Ether and Carbon Dioxide under Atmospheric Pressure, J. Org. Chem., 1993, pp. 6198-6202, vol. 58.
Fleischer et al., Glycerol-, pentaerythritol- and trimethylolpropane-based polyurethanes and their cellulose carbonate composites prepared via the non-isocyanate route with catalytic carbon dioxide fixation, Green Chemistry, 2013, pp. 934-942, vol. 15.
Roshan et al., A biopolymer mediated efficient synthesis of cyclic carbonates from epoxides and carbon dioxide, Green Chemistry, 2012, pp. 2933-2940, vol. 14.
Kawahara et al., Preparation of Carbonated Natural Rubber, J. Polym. Sci. Part A.: Polym. Chem., 2006, pp. 1561-1567, vol. 44.
Aoyagi et al., Convenient Synthesis of Cyclic Carbonates from CO2 and Epoxides by Simple Secondary and Primary Ammonium Iodides as Metal-Free Catalysts under Mild Conditions and Its Application to Synthesis of Polymer Bearing Cyclic Carbonate Moiety, Journal of Polymer Science, Part A: Polymer Chemistry, 2013, pp. 1230-1242, vol. 51.
Andreozzi, et al., Sintesi dei carbonati di alchilene con alogenuri alcalini supportati su carbone attivo, Chimica E L'Industria, Societa Chimica Italiano, Milano It, 1985, vol. 67, No. 9, pp. 481-483.
Liang S. et al., Highly efficient synthesis of cyclic carbonates from CO2 and epoxides over cellulose/KI, Chemical Communications, 2010, vol. 47, No. 7, pp. 2131-2133.

(Continued)

*Primary Examiner* — Taylor V Oh
(74) *Attorney, Agent, or Firm* — James E. Piotrowski

(57) ABSTRACT

The present invention relates to a method for synthesizing cyclocarbonates by reacting an epoxy compound and carbon dioxide at atmospheric pressure and elevated temperature in the presence of a heterogeneous catalyst system comprising an alkali metal halide and silica as well as the use of said catalyst system for the synthesis of cyclocarbonates.

13 Claims, No Drawings

(56) References Cited

OTHER PUBLICATIONS

Takahashi et al., Synergistic hybrid catalyst for cyclic carbonate synthesis: Remarkable acceleration caused by immobilization of homogeneous catalyst on silica, Chemical Communications, 2006, No. 15, pp. 1664-1666.
Han et al., Silica grafted imidazolium-based ionic liquids: efficient heterogeneous catalysts for chemical fixation of $CO_2$ to a cyclic carbonate, Energy & Environmental Science, 2009, vol. 2, No. 12, pp. 1286-1292.
Dai et al., Applied Catalysis A: General, 2009, 366, 2-12.

\* cited by examiner

METHOD FOR SYNTHESIZING CYCLIC CARBONATES

The present invention relates to a method for synthesizing cyclocarbonates by reacting an epoxy compound and carbon dioxide at atmospheric pressure and elevated temperature in the presence of a heterogeneous catalyst system comprising an alkali metal halide and silica as well as the use of said catalyst system for the synthesis of cyclocarbonates.

Two-component bonding agent systems, particularly based on a polyol component and a polyisocyanate component, such as a NCO-terminated polyurethane prepolymer, have long been known in the prior art. They are employed, for example in the metal working industry, the automobile industry, the electrical industry, the packaging industry or the building industry as adhesives, sealants, fillers or castings. A disadvantage of the polyisocyanate component is the moisture sensitivity. Consequently, suitably sealed packaging has to be used for storing these compounds. Once opened, containers usually have to be used up immediately or quickly in order to avoid any loss in quality. Generally, the polyol component has to be carefully dried prior to mixing with the polyisocyanate component, because otherwise, any residual moisture can lead to the formation of unwanted bubbles in the adhesive film, which under certain circumstances can be disadvantageous for the final application.

A further disadvantage for at least some bonding agent systems based on two-component polyurethane adhesives, is the toxicity of monomeric isocyanates, in particular highly volatile and/or easily migratable monomeric diisocyanates, in the polyisocyanate component. The use of products containing a high content of highly volatile diisocyanates requires the user to implement costly protective measures in the workplace, in particular to maintain clean and breathable air, the maximum legally permitted concentration of handled materials as gas, vapor or particulate matter in the air at the workplace being specified (in Germany, for example; by the annually updated "MAK-Wert-Liste der Technischen Regel TRGS 900 des Bundesministeriums for Arbeit and Soziales"). However, free monomeric polyisocyanates can also migrate into the coating or adhesive bond, or even partially into the coated or glued materials. Such migrating ingredients are commonly called "migrates" by technical specialists. On contact with moisture, the isocyanate groups of the migrates are continuously reacted to amino groups.

Migrates are highly undesirable in the packaging industry and particularly in the packaging of foods. On the one hand, the passage of the migrates through the packaging material can lead to contamination of the packaged product; on the other hand, long waiting times are necessary before the packaging material is "migrate-free" and can be used.

Another unwanted effect, which can be caused by the migration of monomeric diisocyanates, is the so-called anti-sealing effect in the production of bags or carrier bags from laminated plastic films. The laminated plastic films often contain slip agents based on fatty acid amides. By reaction of migrated monomeric polyisocyanate with the fatty acid amide and/or moisture, urea compounds with a melting point above the sealing temperature of the plastic films are formed on the surface of the film. This leads to the formation of a urea compound containing layer between the films to be sealed, which hinders the formation of a homogeneous sealing seam.

Alternative products based on compounds with cyclic carbonate groups, so-called non-isocyanate polyurethanes or hybrid non-isocyanate polyurethanes, are known in principle and have been described, for example, in U.S. Pat. No. 8,118,968 and U.S. Pat. No. 7,232,877.

The cyclic carbonates utilized for such alternative products are currently synthesized under high pressure conditions (Fleischer et al., Green Chem., 2013, 15, 934-942), which has the drawback of high energy consumption, requirement of special equipment and high risks for the involved personnel. When homogeneous catalysis is used, work-up after production is needed to separate the catalyst from the product (Fleischer et al., vide supra; Roshan et al., Green Chem., 2012, 14, 2933-2940; Kihara et al., J. Org. Chem., 1993, 58, 6198-6202). Homogeneous catalysis of the incorporation of carbon dioxide into epoxy compounds using an alkali metal iodide as a catalyst is for example described in DE 3600602 A1. Compared with homogeneous catalysts, heterogeneous catalysts can be easily separated and recovered from the reaction mixture after the reaction is completed, which is desirable from economic, environmental, and industrial considerations. However, heterogeneous catalysts suffer from the drawback that the catalytic species are often not commercially available and have to be synthesized (Han et al., Energy environ. Sci., 2009, 2, 1286-1292; Dai et al., Applied Catalysis A: General, 2009, 366, 2-12; Motokura et al., Green Chem., 2009, 11, 1876-1880).

The object of the present invention was thus to provide a heterogeneous catalyst system that overcomes the drawbacks of existing systems and provides for a simple and effective method for the synthesis of cyclocarbonates while being easily separable and recoverable from the reaction mixture after completion of the reaction. The present invention meets this need by providing a heterogeneous catalyst system based on an alkali metal halide selected from alkali metal iodide or bromide and silica gel as a solid support material. Surprisingly, it has been found that using silica as a solid support material the conversion rates and times of alkali metal iodide or alkali metal bromide, specifically sodium iodide or lithium bromide, catalyzed cyclic carbonate synthesis reactions can be significantly increased.

In a first aspect, the present invention therefore relates to a method for synthesizing a cyclocarbonate, comprising reacting at least one epoxy compound and carbon dioxide at atmospheric pressure and a temperature in the range of 100 to 150° C. in the presence of a heterogeneous catalyst system, the catalyst system comprising (a) at least one alkali metal halide selected from the group consisting of alkali metal iodides and alkali metal bromides, preferably selected from the group consisting of lithium iodide (LiI), sodium iodide (NaI), potassium iodide (KI), lithium bromide (LiBr), sodium bromide (NaBr) and potassium bromide (KBr), and (b) silica ($SiO_2$).

In another aspect, the present invention is also directed to the use of a heterogeneous catalyst system comprising (a) at least one alkali metal halide selected from the group consisting of alkali metal iodides and alkali metal bromides, preferably selected from the group consisting of lithium iodide (LiI), sodium iodide (NaI), potassium iodide (KI), lithium bromide (LiBr), sodium bromide (NaBr) and potassium bromide (KBr), and (b) silica ($SiO_2$) for catalyzing the reaction of at least one epoxy compound with carbon dioxide at atmospheric pressure and a temperature in the range of from 100 to 150° C., preferably 120 to 140° C., to form a cyclocarbonate.

Preferred embodiments are set out in the dependent claims.

"One or more", as used herein, relates to at least one and comprises 1, 2, 3, 4, 5, 6, 7, 8, 9 or more of the referenced species. Similarly, "at least one" means one or more, i.e. 1, 2, 3, 4, 5, 6, 7, 8, 9 or more. "At least one", as used herein in relation to any component, refers to the number of chemically different molecules, i.e. to the number of different types of the referenced species, but not to the total number of molecules. For example, "at least one epoxy compound" means that at least one type of molecule falling within the definition for an epoxy compound is used but that also two or more different molecule types falling within this definition can be present, but does not mean that only one molecule of said epoxy compound is present.

If reference is made herein to a molecular weight, this reference refers to the number average molecular weight $M_n$, if not explicitly stated otherwise. The number average molecular weight $M_n$ can be determined by gel permeation chromatography according to DIN 55672-1:2007-08 with THF as the eluent. If not stated otherwise, all given molecular weights are those determined by GPC. The weight average molecular weight $M_w$ can be determined by GPC, as described for $M_n$.

If reference is made herein to a viscosity, this reference refers to a viscosity as determined using an Anton Paar, Physica MCT51 viscosimeter (plate-plate system: position 0.5 mm (gap), spindle diameter 25 mm) at a shear rate of 100 $s^{-1}$.

All percentages given herein in relation to the methods relate to weight % relative to the total weight of the reaction mixture or the epoxy compound, as indicated, if not explicitly stated otherwise.

"About" or "approximately" as used herein in connection with a numerical value refers to the numerical value ±10%, preferably ±5%. "About 100° C." thus relates to 100±10, preferably 100±5° C.

"NCO", as used herein, refers to the isocyanate group —N═C═O.

"Cyclocarbonate", as used herein, relates to alkylene carbonates, i.e. compounds that comprise at least one 2-oxo-1,3-dioxolane group.

The present invention is based on the inventors' surprising finding that the incorporation of carbon dioxide into epoxides can be significantly improved with respect to reaction times, if an alkali metal halide catalyst is used in combination with silica as a solid support.

The epoxy compounds that can be reacted with carbon dioxide according to the methods described herein generally comprise at least one terminal 1,2-epoxy group.

Suitable compounds include higher aliphatic epoxides, such as hexene-, octene-, dodecene-1-oxide, glycidol and epihalogenhydrins of formula (1)

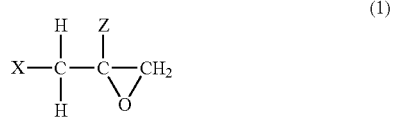

(1)

wherein Z represents hydrogen, methyl or ethyl, and X represents a halogen atom or an —OH group. Examples for such epihalogenhydrins include epichlorohydrin, epibromohydrin, 1,2-epoxy-2-methyl-3-chloropropane, and 1,2-epoxy-2-ethyl-3-chloropropane.

Further epoxy compounds that can be used in accordance with the present invention include epoxy compounds that have at least one terminal epoxy group, preferably epoxy compounds having at least one substituted or unsubstituted glycidylether or glycidylester group as well as epoxylated polyunsaturated compounds and amide or urethane group containing epoxides.

Preferred are epoxy compounds that comprise at least one substituted or unsubstituted glycidylether group of formula (2)

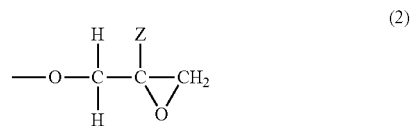

(2)

wherein Z represents hydrogen, methyl or ethyl. Examples for such compounds include, but are not limited to, glycidyl and polyglycidyl ethers of phenol or polyhydric phenols, having one or more aromatic rings, and novolacs, and polyglycidyl ethers of polyols, including those obtainable by addition of polyhydric phenols, comprising one or more aromatic rings, to alkylene oxides having 2-4 carbon atoms. Useful phenols include phenol, the different cresols, resorcin, hydroquinone, pyrogallol, phloroglucin, 1,5-, 2,7-, 2,6-dihydronaphthenes, 2,2-bis(4-hydroxyphenyl)propane and bis(4-hydroxyphenyl)methane (bisphenol A and F, respectively), and 2,4'-dihydroxydiphenylmethane. Polyols that can be reacted to glycidylethers include, but are not limited to, ethylene glycol, propylene glycol, butylene glycol, neopentyl glycol, hexylene glycol, glycerol, trimethylolethane, trimethylolpropane, pentaerythritol, sugar alcohols, or mixtures of two or more thereof. Further polyols that can be reacted to glycidylethers include, but are not limited to, polyether polyols, obtainable by reaction of low molecular weight polyfunctional alcohols with alkylene oxides. The alkylene oxides preferably have 2 to 4 C atoms. The reaction products of ethylene glycol, propylene glycol, butylene glycol, hexylene glycol, 2,2-bis(4-hydroxyphenyl)propane, bis(4-hydroxyphenyl)methane or 2,4'-dihydroxydiphenylmethane with ethylene oxide, propylene oxide or butylene oxide, or mixtures of two or more thereof are, for example, suitable. The reaction products of polyfunctional alcohols, such as glycerol, trimethylolethane or trimethylolpropane, pentaerythritol or sugar alcohols, or mixtures of two or more thereof, with the stated alkylene oxides to form polyether polyols are furthermore also suitable. Further polyols which may be used for the purposes of the invention are obtained by polymerization of tetrahydrofuran (poly-THF). Preferred polyols are polyalkylene glycol homo- or copolymers, preferably polypropylene glycol homo- or copolymers, polyethylene glycol homo- or copolymers, polytetramethylene glycol homo- or copolymers, or polypropylene glycol/polyethylene glycol block copolymers. Particularly preferred polyols are polypropylene glycol, polyethylene glycol and butylene glycol, such as 1,4-butanediol.

Also suitable are (plasticized) epoxy resins with terminal epoxy groups, obtainable by partially reacting the epoxy group of epoxy resins comprising at least two epoxy groups with —OH and/or —COOH group containing substances, such as polyhydric alcohols, including the above-described polyols, polycarboxylic acids or hydroxyl or carboxyl group-containing polyesters.

Further suitable epoxy compounds include glycidyl esters of saturated or ethylenically unsaturated carboxylic acids with at least one substituted or unsubstituted glycidylester group of formula (3)

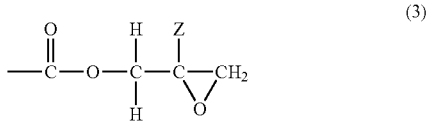

(3)

wherein Z represents hydrogen, methyl or ethyl. The acids are aliphatic or aromatic, saturated or unsaturated mono- or polycarboxylic acids, e.g. acrylic acid, methacrylic acid, adipic acid, the different phthalic acids, tetra- and hexahydrophthalic acid and the like.

Also included are epoxy resins obtained by copolymerisation of glycidylmethacrylic acid ester with other copolymerizable monomers, such as styrene and (meth)acrylic acid esters.

Moreover, the epoxy compounds include also amide or urethane group-containing epoxides, such as triglycidylisocyanurate, glycidol-capped hexamethylenediisocyanate or glycidol-capped NCO-terminated polyurethanes.

In various embodiments, the epoxy compound is a multifunctional epoxy compound, i.e. comprises at least two epoxy groups, typically terminal epoxy groups. In various embodiments, the epoxy compound is a bifunctional compound, i.e. comprises two epoxy groups, preferably terminal epoxy groups. Preferred are glycidyl ethers of a polyol, in particular a diol, such as 1,4-butanediol, or a polyalkylene glycol, such as polyethylene glycol or polypropylene glycol. Particularly preferred are diglycidyl ethers of polyethylene, polypropylene and diols, such as 1,4-butanediol.

In various embodiments, the epoxy compound is an aliphatic epoxy resin, in particular a polyglycidyl ether of an aliphatic polyol, such as those listed above.

In various embodiments, the epoxy compounds have a molecular weight $M_n$ of 100 to 1000 g/mol, preferably 200 to 800 g/mol, in particular 400 to 600 g/mol. Such compounds include diglycidyl ethers of polyethylene glycol and polypropylene glycol with 2 to 10 monomeric units.

The afore-described epoxy compounds may be used individually or in combination. It is preferred that the epoxy compounds are liquid epoxy resins. "Liquid", as used in this context, means that the epoxy resins are liquid at the reaction temperature, i.e. temperatures of 100° C. or more, and at atmospheric pressure. In preferred embodiments, the epoxy compounds used are liquid at a temperature of about 50° C., more preferably at about ambient temperature, i.e. about 20° C. The liquid epoxy resins preferably have a viscosity of less than 110 mPas at 25° C. and atmospheric pressure.

In the described methods, the reaction is carried out at a temperature of about 100 to about 150° C., preferably at a temperature in the range of about 130 to about 140° C. The described methods are carried out at atmospheric pressure, typically under a carbon dioxide atmosphere that provides the carbon dioxide for the reaction with the epoxide. The carbon dioxide can be flushed into the reaction vessel, for example continuously, and may be provided by sublimation of dry ice or from a pressurized container.

The carbon dioxide may be fed directly into the liquid epoxy compound, for example by use of an inlet pipe, typically while stirring the liquid resin, or may simply be flushed into the reaction vessel. To increase the contact between the epoxide and the carbon dioxide, the epoxide is preferably in liquid form and agitated, preferably stirred. If the epoxide is not liquid at the reaction temperature, a suitable solvent may be used to dissolve the epoxide. Suitable solvents include, but are not limited to toluene, xylene, various hydrocarbons and mixtures thereof, dioxane, tetrahydrofurane, and other solvents that are inert towards the epoxy compound.

The heterogeneous catalyst system comprises at least one alkali metal halide selected from the group consisting of alkali metal iodides and alkali metal bromides, preferably selected from the group consisting of lithium iodide (LiI), sodium iodide (NaI), potassium iodide (KI), lithium bromide (LiBr), sodium bromide (NaBr) and potassium bromide (KBr). Particularly preferred are sodium iodide, potassium iodide, and lithium iodide.

The alkali metal halides are combined with a solid support material, namely silica ($SiO_2$), preferably silica gel. The silica is, in various embodiments, in particulate form and comprises particles of a mean diameter in the range of from 20 to 100 μm, preferably 35 to 70 μm. "Mean diameter", refers to the arithmetic mean of the particle diameters, with the particles being roughly spherical in shape, and is determined according to ISO 13320:2009. In preferred embodiments, the silica particles used do not contain significant amounts of particles with a mean diameter <10 μm, i.e. not more than 10%, preferably not more than 5% of the particles have diameters below 10 μm. It is generally preferred to use silica with a high surface area, preferably a surface area of more than 200 $m^2/g$, more preferably about 500 $m^2/g$ or more, as determined by N2 adsorption and described by C. Ting, et al. (C. Ting et al., Chinese Journal of Catalysis, 2012, 3, 416).

In the methods, according to the invention, the heterogeneous catalyst system preferably comprises relative to the epoxy compound 0.5 to 5% by weight, preferably 1.5 to 2.5% by weight, of the alkali metal halide. Similarly, in various embodiments, the catalyst system comprises 0.5 to 5% by weight, preferably 1.5 to 2.5% by weight, of the silica relative to the amount of the epoxy compound. The alkali metal halide and the silica are preferably used in a weight ratio of 2:1 to 1:2, preferably about 1:1.

The reaction is typically carried out for a time period between about 30 minutes and 24 hours until the conversion is complete. The conversion of the epoxide can be monitored by $^1$H-NMR or IR spectroscopy.

The invention is also directed to the use of a heterogeneous catalyst system comprising (a) at least one alkali metal halide selected from the group consisting of alkali metal iodides and alkali metal bromides, preferably selected from the group consisting of lithium iodide (LiI), sodium iodide (NaI), potassium iodide (KI), lithium bromide (LiBr), sodium bromide (NaBr) and potassium bromide (KBr), and (b) silica ($SiO_2$) for catalyzing the reaction of at least one epoxy compound with carbon dioxide at atmospheric pressure and a temperature in the range of from about 100 to about 150° C., preferably about 120 to about 140° C., to form a cyclocarbonate.

All embodiments disclosed herein in relation to the described processes and methods are similarly applicable to the claimed uses and vice versa.

The cyclocarbonates synthesized according to the methods described herein can be used in various applications and formulations, all of which are known to those skilled in the art and include for example the formulations and uses described in U.S. Pat. No. 8,118,968.

All documents cited herein are hereby incorporated by reference in their entirety. The invention is further illustrated by the following examples without being limited thereto.

EXAMPLES

Comparative Example 1: Reaction Between Polyethyleneglycol Diglycidyl Ether (PEGDE) and SiO$_2$

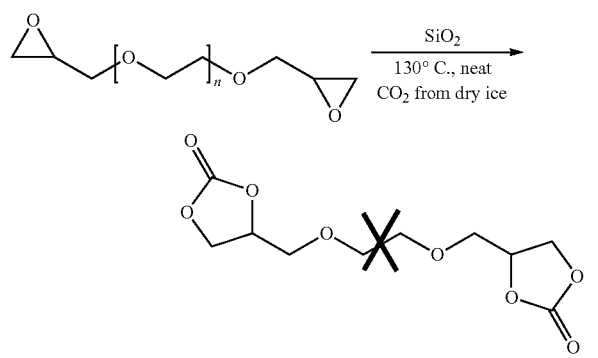

Polyethyleneglycol diglycidyl ether (PEGDE, 1 g, M$_n$=500 g/mol) and SiO$_2$ (20 mg, silica gel mesh 60) were stirred in a glass round bottom flask under CO$_2$ atmospheric pressure (the air inside the flask was displaced by CO$_2$ with the help of carbon dioxide filled balloons) at 130° C.

No cyclic carbonate was observed by means of $^1$H-NMR or IR spectroscopy after 4 h. Only hydrolysis products of the epoxides were detected after 8 h.

Comparative Example 2: Reaction Between Polyethyleneglycol Diglycidyl Ether (PEGDE) and NaI

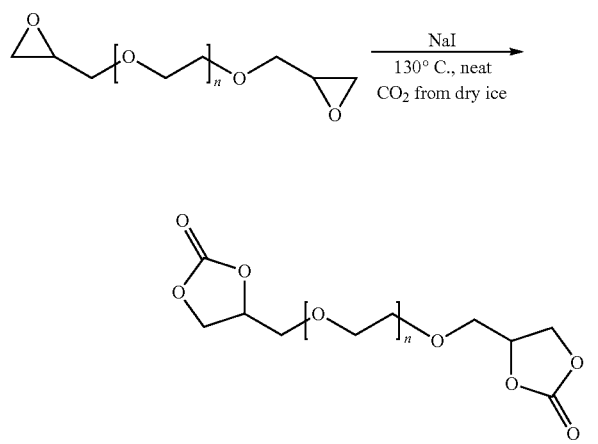

Polyethyleneglycol diglycidyl ether (PEGDE, 1 g, M$_n$=500 g/mol) and NaI (20 mg) were stirred in a glass round bottom flask under CO$_2$ atmospheric pressure (the air inside the flask was displaced by CO$_2$ with the help of carbon dioxide filled balloons) at 130° C.

100% conversion into the corresponding cyclic carbonate was observed after 4 h by means of $^1$H-NMR and IR spectroscopy. No side products were observed.

Example 3: Reaction Between Polyethyleneglycol Diglycidyl Ether (PEGDE), SiO$_2$, and NaI

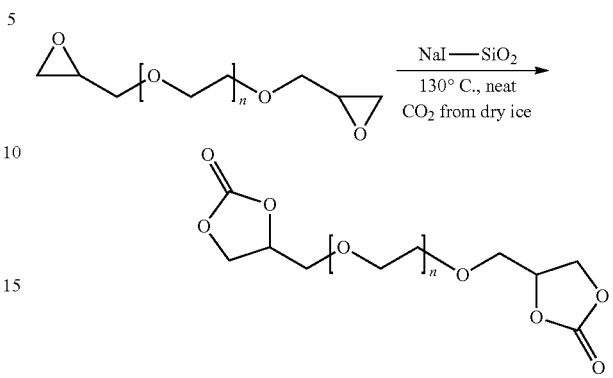

Polyethyleneglycol diglycidyl ether (PEGDE, 1 g, M$_n$=500 g/mol), SiO$_2$ (20 mg) and NaI (20 mg) were stirred in a glass round bottom flask under CO$_2$ atmospheric pressure (the air inside the flask was displaced by CO$_2$ with the help of carbon dioxide filled balloons) at 130° C.

100% conversion into the corresponding cyclic carbonate was observed after 2 h by means of $^1$H-NMR and IR spectroscopy. No side products were observed.

Comparative Example 4: Reaction Between Polyethyleneglycol Diglycidyl Ether (PEGDE), and LiBr

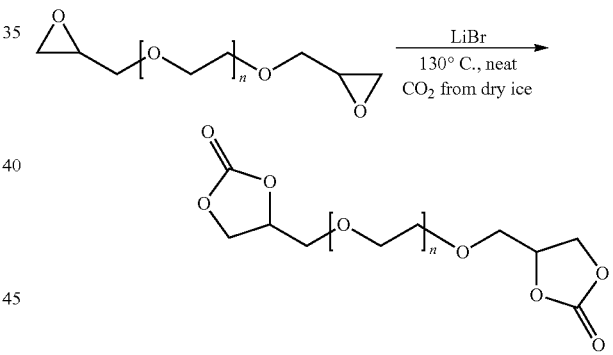

Polyethyleneglycol diglycidyl ether (PEGDE, 1 g, M$_n$=500 g/mol) and LiBr (20 mg) were stirred in a glass round bottom flask under CO$_2$ atmospheric pressure (the air inside the flask was displaced by CO$_2$ with the help of carbon dioxide filled balloons) at 130° C.

100% conversion into the corresponding cyclic carbonate was observed after 2 h by means of $^1$H-NMR and IR spectroscopy. No side products were observed.

Example 5: Reaction Between Polyethyleneglycol Diglycidyl Ether (PEGDE), SiO$_2$, and LiBr

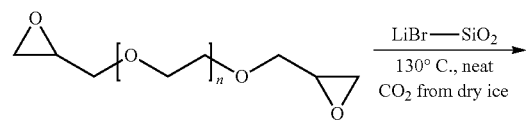

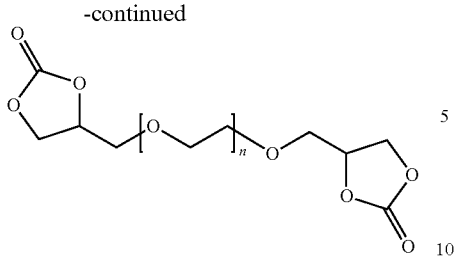

Polyethyleneglycol diglycidyl ether (PEGDE, 1 g, $M_n$=500 g/mol), $SiO_2$ (20 mg) and LiBr (20 mg) were stirred in a glass round bottom flask under $CO_2$ atmospheric pressure (the air inside the flask was displaced by $CO_2$ with the help of carbon dioxide filled balloons) at 130° C.

100% conversion into the corresponding cyclic carbonate was observed after 1 h by means of $^1$H-NMR and IR spectroscopy. No side products were observed.

Example 6: Reaction Between D.E.R.™ 736, $SiO_2$, and NaI

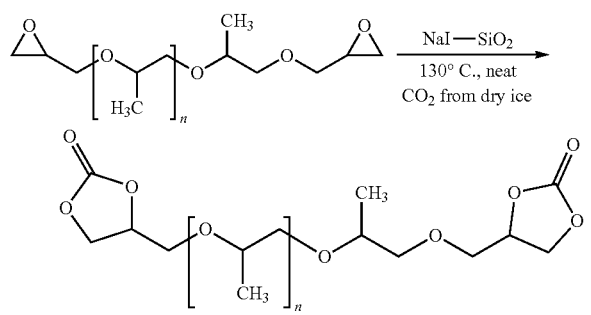

D.E.R.™ 736 from The Dow Chemical Company (1 g), $SiO_2$ (20 mg) and NaI (20 mg) were stirred in a glass round bottom flask under $CO_2$ atmospheric pressure (the air inside the flask was displaced by $CO_2$ with the help of carbon dioxide filled balloons) at 130° C.

100% conversion into the corresponding cyclic carbonate was observed after 8 h by means of $^1$H-NMR and IR spectroscopy. No side products were observed.

Example 7: Reaction Between D.E.R.™ 736, $SiO_2$, and LiBr

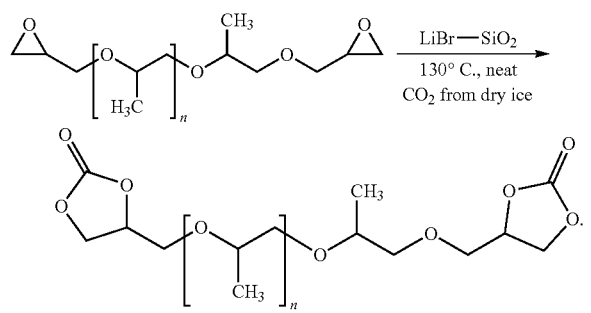

D.E.R.™ 736 (1 g), $SiO_2$ (20 mg) and LiBr (20 mg) were stirred in a glass round bottom flask under $CO_2$ atmospheric pressure (the air inside the flask was displaced by $CO_2$ with the help of carbon dioxide filled balloons) at 130° C.

100% conversion into the corresponding cyclic carbonate was observed after 6 h by means of $^1$H-NMR and IR spectroscopy. Some side products derived from degradation of epoxide moieties were detected.

Example 8: Reaction Between 1,4-butanediol diglycidyl ether, $SiO_2$, and NaI

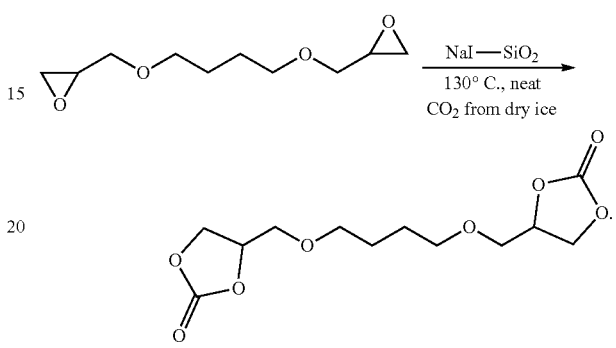

1,4-butanediol diglycidyl ether (1 g), $SiO_2$ (20 mg) and NaI (20 mg) were stirred in a glass round bottom flask under $CO_2$ atmospheric pressure (the air inside the flask was displaced by $CO_2$ with the help of carbon dioxide filled balloons) at 130° C.

100% conversion into the corresponding cyclic carbonate was observed after 2 h by means of $^1$H-NMR and IR spectroscopy. No side products were observed.

Example 9: Reaction Between 1,4-butanediol diglycidyl ether, $SiO_2$, and LiBr

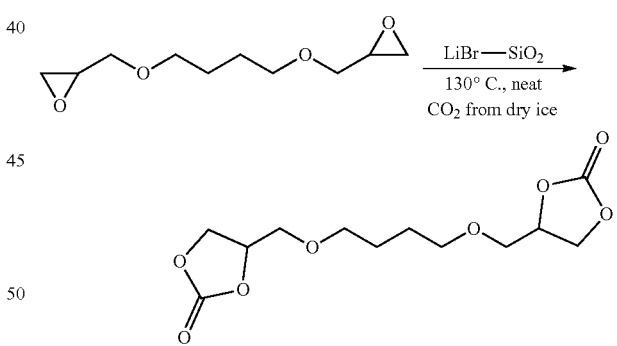

1,4-butanediol diglycidyl ether (1 g), $SiO_2$ (20 mg) and LiBr (20 mg) were stirred in a glass round bottom flask under $CO_2$ atmospheric pressure (the air inside the flask was displaced by $CO_2$ with the help of carbon dioxide filled balloons) at 130° C.

100% conversion into the corresponding cyclic carbonate was observed after 2 h by means of $^1$H-NMR and IR spectroscopy. Some side products derived from degradation of epoxide moieties were detected.

The invention claimed is:

1. A method for synthesizing a cyclocarbonate, comprising:
   providing at least one epoxy compound;
   providing carbon dioxide;

providing a heterogeneous catalyst system;
reacting the at least one epoxy compound and the carbon dioxide at atmospheric pressure and a temperature in the range of 100 to 150° C. in the presence of the heterogeneous catalyst system, wherein the catalyst system comprises
(a) at least one alkali metal halide selected from the group consisting of alkali metal iodides and alkali metal bromides, and
(b) silica ($SiO_2$).

2. The method according to claim 1, wherein the at least one alkali metal halide is selected from the group consisting of lithium iodide (LiI), sodium iodide (NaI), potassium iodide (KI), lithium bromide (LiBr), sodium bromide (NaBr), potassium bromide (KBr) and combinations thereof.

3. The method according to claim 1, wherein the at least one epoxy compound
(a) is a multifunctional epoxy resin; and/or
(b) is a liquid epoxy resin; and/or
(c) is an aliphatic epoxy resin; and/or
(d) has a molecular weight of 200 to 1000 g/mol.

4. The method according to claim 3, wherein the at least one epoxy compound (d) has a molecular weight of 400 to 600 g/mol.

5. The method according to claim 1, wherein the reaction temperature is in the range of 120 to 140° C.

6. The method according to claim 1, wherein the carbon dioxide is provided in form of carbon dioxide gas, wherein the reaction is carried out under a carbon dioxide atmosphere.

7. The method according to claim 4, wherein the carbon dioxide is provided in solid form (dry ice) and the method further comprises allowing the solid carbon dioxide to sublimate to gas in the reaction.

8. The method according to claim 1, wherein the heterogeneous catalyst system comprises 0.5 to 5% by weight of the alkali metal halide relative to the epoxy compound and 0.5 to 5% by weight of the silica relative to the epoxy compound.

9. The method according to claim 1, wherein the heterogeneous catalyst system comprises 1.5 to 2.5% by weight of the alkali metal halide relative to the epoxy compound and 1.5 to 2.5% by weight of the silica relative to the epoxy compound.

10. The method according to claim 1, wherein the silica is in form of silica gel particles having a mean diameter of 35 to 70 μm.

11. The method according to claim 3, wherein the at least one epoxy compound is a liquid epoxy resin having a viscosity of less than 110 mPas at 25° C.

12. The method according to claim 1 wherein the at least one epoxy compound comprises at least one terminal 1,2-epoxy group.

13. The method according to claim 1 wherein the at least one epoxy compound is selected from:
formula (1)

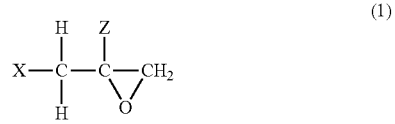

wherein Z represents hydrogen, methyl or ethyl, and X represents a halogen atom or an —OH group; or
formula (2)

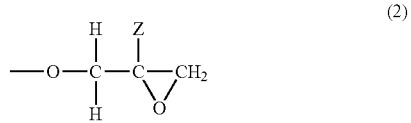

wherein Z represents hydrogen, methyl or ethyl; or
the at least one epoxy compound is a glycidyl ester of saturated or ethylenically unsaturated carboxylic acids with at least one substituted or unsubstituted glycidylester group of formula (3)

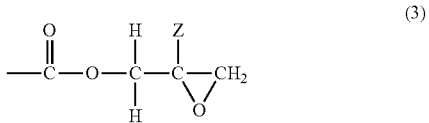

wherein Z represents hydrogen, methyl or ethyl.

* * * * *